United States Patent [19]
Hornkvist

[11] Patent Number: 4,933,340
[45] Date of Patent: Jun. 12, 1990

[54] METHOD FOR THE TREATMENT OF OBESITY

[75] Inventor: Per-Erik Hornkvist, Göteborg, Sweden

[73] Assignee: Imperial Chemical Industries plc, London, England

[21] Appl. No.: 934,996

[22] Filed: Nov. 26, 1986

[30] Foreign Application Priority Data

Dec. 4, 1985 [GB] United Kingdom ............... 8529885

[51] Int. Cl.$^5$ .......................................... A61K 31/535
[52] U.S. Cl. ................................................ 514/237.5
[58] Field of Search ............. 544/162; 514/245, 237.5

[56] References Cited

U.S. PATENT DOCUMENTS 3,806,595 5/1974 Jaggers et al. ................... 514/239.2

FOREIGN PATENT DOCUMENTS 2002748 2/1979 United Kingdom .

OTHER PUBLICATIONS

Arch et al., *Nature*, vol. 309 (May 19, 1984), pp. 163–165.
Chem. Abstracts, vol. 102(1), abst. No. 115R (Jan. 1985).
Chem. Abstracts, vol. 103(5), abst. No. 32229t (Aug. 1985).
Biological Abstracts, vol. 68(6), Abst. No. 36886 (Sep. 1979).
Ichihara, K. et al., "Metabolic Responses to a New Beta-Adrenoceptor Agonist, ICI 118,587, in Conscious Rats", Pharmacology, 27, (1983), pp. 202–210.
Vik-Mo, H. et al., "Comparative Effects of Dobutamine and Corwin, A $B_1$-Adrenergic Partial Agonist, in Experimental Left Ventricular Failure", J. Cardiovascular Pharmacology, vol. 7, No. 4, Jul./Aug. 1985, pp. 784–790.
*The Merck Manual of Diagnosis and Therapy,* eds. Berkow, R. et al., Merck & Sharp and Dohme Research Laboratories, 14th Ed., (1982), pp. 916–920.
Br. J. Pharmac. (1982), 77, 381–388.
British Medical Journal, vol. 296, Apr. 30, 1988, pp. 1217–1220.

*Primary Examiner*—Mary C. Lee
*Assistant Examiner*—MarySue Howard
*Attorney, Agent, or Firm*—Cushman, Darby & Cushman

[57] ABSTRACT

The invention concerns the use of N-(2-[RS-2-hydroxy-3-(4-hydroxyphenoxy)propylamino]ethyl)-morpholinoformamide or a salt thereof in the production of a medicament for the treatment of obesity and/or related conditions in warm-blooded animals including man.

6 Claims, No Drawings

METHOD FOR THE TREATMENT OF OBESITY

This invention concerns a therapeutic agent for use in the treatment of obesity and/or related conditions such as obesity of maturity onset diabetes, affecting warm-blooded animals, especially humans or domestic animals. More particularly, the invention concerns the novel use of the known pharmaceutical agent xamoterol, its S-enantiomer or a salt in the treatment of obesity and/or related conditions in humans or domestic animals, and in the manufacture of a new medicament for such use.

According to the invention there is provided a method for the treatment of obesity and/or related conditions in warm-blooded animals, such as humans or domestic animals which comprises the administration of a therapeutically effective amount of a therapeutic agent selected from N-(2-[RS-2-hydroxy-3-(4-hydroxyphenoxy)propylamino]ethyl)morpholinoformamide of formula I (also known as xamoterol) and the S-laevorotatory enantiomer thereof, or of a pharmaceutically acceptable acid-addition salt of said agent, to humans or domestic animals requiring such treatment.

Particularly suitable pharmaceutically acceptable acid-addition salts include, for example, salts derived from a suitable inorganic acid, such as hydrochloric, hydrobromic, phosphoric and sulphuric acids, and salts derived from a suitable organic acid, such as oxalic, fumaric, lactic, acetic, salicylic, citric, benzoic, 2-naphthoic and adipic acid, 1,1-methylene-bis(2-hydroxy-3-naphthoic acid), and from an acidic synthetic resin, such as a sulphonated polystyrene resin.

A preferred pharmaceutically-acceptable salt is, for example, the hydrochloride, hydrobromide or fumarate salt and according to a particularly preferred aspect of the invention the therapeutic agent is the known agent xamoterol (that is the the compound of formula I) administered as its fumarate salt.

Xamoterol is known to be a cardioselective beta-adrenoceptor partial agonist which is well tolerated and has a relatively long duration of action (A. Nuttall and H. M. Snow, *British J. Pharmacology*, 1982, 77, 381–388). The preparation of the compound of formula I, the S-laevorotatory enantiomer thereof, and the pharmaceutically-acceptable salts thereof, is described in United Kingdom Patent GB2002748B. The satisfactory treatment of obesity without untoward side-effects is a difficult problem. We have now discovered that xamoterol increases the rate of metabolism in dogs without untoward effects on the heart and peripheral vasculature so that it is of use in the treatment of obesity and/or related conditions in humans or domestic animals, such as cats, dogs, pigs and/or cattle.

When used in the treatment of obesity or related conditions, the therapeutic agent (that is the compound of formula I or its S-laevorotatory enantiomer) will generally be administered as a pharmaceutically-acceptable acid-addition salt and, preferably, as its fumarate salt, conveniently in the form of a conventional pharmaceutical composition, for example such as is described in UK Patent GB 2002748B. It is expected that, in man, a daily dose of therapeutic agent in the range, for example, 50–600 mg p.o. or 3 mg–20 mg i.v. will be administered, if necessary in divided doses, in order to achieve the required reduction in obesity. However, it will be understood that the actual therapeutic dose administered will necessarily be varied according to the age, sex and weight of the patient or animal under treatment, according to principles well understood by those skilled in the medical and veterinary arts.

The invention also provides the use of xamoterol or its S-laevoratotory enantiomer, or of a pharmaceutically acceptable acid-addition salt thereof, in the manufacture of a novel medicament for use in the treatment of obesity and/or related conditions affecting warm-blooded animals, especially humans or domestic animals.

The effects of xamoterol in dogs under laboratory conditions and in humans are described in the following Examples, which illustrate the basis for the invention:

EXAMPLE 1

Four male beagle dogs (average weight 16.6 kg) were maintained in a controlled, ventilated environment through which air was drawn at a rate of 40 liters/minute into an open circuit oxygen consumption apparatus, comprising a conventional paramagnetic oxygen analyser coupled to a mass flowmeter, to determine the amount of oxygen consumed per minute. The resting oxygen consumption rate was first determined 3 hours after the last meal. The test compound was then administered sub-cutaneously. After 30 minutes the oxygen consumption rate was again measured and the change in rate relative to the resting rate determined.

Using this procedure, the cardio-selective beta-adrenoceptor partial agonist xamoterol (administered as its fumarate salt at 0.5 mg/kg sub-cutaneously) produced an increase over resting oxygen consumption of 8.24 ml/min/kg $^{0.75}$ ($p < 0.005$) whereas the non-selective beta-adrenoceptor agonist isoprenaline sulphate (administered at 0.5 mg/kg sub-cutaneously) produced an increase over resting oxygen consumption of 19.94 ml/min/kg $^{0.75}$ ($p < 0.001$), the average resting oxygen consumption being 25 ml./min./kg $^{0.75}$.

EXAMPLE 2

Male beagle dogs (average weight 16.6 kg.) were fasted overnight, anaesthetised with pentabarbitone and cannulated for measurement of heart rate and blood pressure by conventional methods. Oxygen consumption was measured using the procedure described in Example 1 using an air flow rate of 25 liter/minute. The effect of a test agent administered by intravenous infusion was then compared with the effect of noradrenaline.

Xamoterol, infused as an aqueous solution of its fumarate salt by increments up to 37.5 $\mu$g/kg/minute, produced a peak 17.3% increase in resting oxygen consumption (i.e. metabolic rate) compared to a challenge of noradrenaline sulphate infused as an aqueous solution at 0.5 $\mu$g/kg/minute which produced a 24.5% increase in resting oxygen consumption. However, the xamoterol infusion resulted in a fall in diastolic blood pressure of 5 mm. Hg. coupled with an increase over resting heart rate of 37 beats/minute. By contrast isoprenaline sulphate infused as an aqueous solution by increments up to 3.75 $\mu$g/kg/minute caused a 72% increase in resting oxygen consumption compared to a challenge of noradrenaline sulphate infused as an aqueous solution at 0.5 $\mu$g/kg/minute which produced a 27.2% increase in resting oxygen consumption. This was associated with a fall in diastolic blood pressure of 52 mm Hg and an increase over resting heart rate of 60 beats/minute. No toxic or other untoward effects were observed in Examples 1 and 2 following administration of xamoterol as its fumarate salt.

EXAMPLE 3

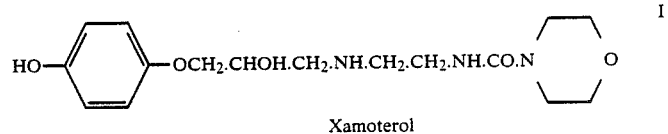

Xamoterol

A clinical evaluation of the effects of xamoterol dosed as its furmate salt intravenously via an antecubital vein was carried out in obese women patients (that is women having a body mass index [mass (kg)/height (m)$^2$] of >30 kb m$^{-2}$).

On four separate days at least one week apart the patients received (a), saline infusion or (b), saline followed by cumulative xamoterol fumarate bolus infusions in saline at (i) 30, (ii) 60 and (iii) 120 μg/kg fat free mass to achieve plasma levels of approximately 40, 100 and 200 ng/ml respectively. Throughout each infusion period oxygen consumption and carbon dioxide production were measured using a ventilated hood, open circuit indirect calorimeter (Sjostrom et alia, *American J. Physiol*, 1983, 243 E431-442) for determination of metabolic rate. The day before each test, patients were required to consume a recommended quantity of food calculated from their individual maintenance engergy requirements and containing 45% carbohydrate, 15% protein and 40% fat. Following an overnight fast and after a period of equilibration basal metabolic rate was then determined followed by the sequence of intravenous infusions for that particular experimental day.

Using this procedure, the following results were obtained:

|  | % Increase over basal metabolic rate | | | |
| --- | --- | --- | --- | --- |
|  | No of | Cumulative Doses | | |
| Treatment | Patients | (i) | (ii) | (iii) |
| (a) Saline | 6 | 1.6 | 0.9 | 1.1 |
| (b) Saline + xamoterol fumarate | 6 | 6.0 | 6.1 | 7.2 |

No untoward side-effects (and in particular no adverse effect on the heart) were observed during this clinical evaluation.

These results demonstrate that xamoterol, administered intravenously as its fumarate salt, produces a significant increase in metabolic rate. [Note: A 7% increase over basal metabolic rate is expected to produce a weight loss of at least 7 kg during a treatment period of 12 months.]

What we claim is:
1. A method for the treatment of obesity and/or related conditions in a warm-blooded animal requiring such treatment which comprises administering to said animal an effective amount of a therapeutic agent selected from N-(2-[RS-2-hydroxy-3-(4-hydroxyphenoxy)propylamino]ethyl)morpholinoformamide

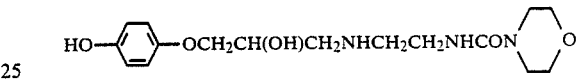

and the S-laevorotatory enantiomer thereof, or a pharmaceutically acceptable acid addition salt thereof.

2. The method as claimed in claim 1 wherein the therapeutic acid is xamoterol or a pharmaceutically acceptable acid addition salt thereof.

3. The method as claimed in claim 2 wherein the therapeutic agent is xamoterol or its salt with hydrochloric, hydrobromic or fumaric acid.

4. The method as claimed in claim 3 wherein the therapeutic agent is xamoterol or its fumarate salt.

5. A method for the treatment of obesity and/or related conditions in a human requiring such treatment which comprises administering to said human an effective amount of a therapeutic agent selected from N-(2-[RS-2-hydroxy-3-(4-hydroxyphenoxy)propylamino]ethyl)morpholinoformamide

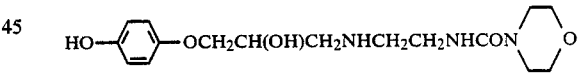

and the S-laevorotatory enantiomer thereof, or a pharmaceutically acceptable acid addition salt thereof.

6. The method as claimed in claim 5 wherein the therapeutic agent is xamoterol or its fumarate salt.

* * * * *